United States Patent [19]

King et al.

[11] Patent Number: 4,753,943

[45] Date of Patent: Jun. 28, 1988

[54] ALGICIDAL AND FUNGICIDAL 2-HALOALKYL-3-OXO-4-SUBSTITUTED QUINAZOLINE

[75] Inventors: William F. King; Malcolm S. Singer, both of Novato, Calif.

[73] Assignee: Chevron Research Company, San Francisco, Calif.

[21] Appl. No.: 306,796

[22] Filed: Sep. 29, 1981

[51] Int. Cl.[4] .................. A01N 43/54; C07D 239/76
[52] U.S. Cl. ........................ 514/259; 71/67; 544/283
[58] Field of Search ................ 544/283; 424/251; 514/259

[56] References Cited

U.S. PATENT DOCUMENTS

| | | | |
|---|---|---|---|
| 2,893,992 | 7/1959 | Sternback | 544/283 |
| 3,051,701 | 8/1962 | Reeder et al. | 544/283 |
| 3,121,074 | 2/1964 | Keller et al. | 544/283 |
| 3,121,075 | 2/1964 | Keller et al. | 544/283 |
| 3,138,586 | 6/1964 | Wuest | 544/283 |
| 3,267,110 | 8/1966 | Pachter et al. | 544/283 |
| 3,297,698 | 1/1967 | Metlesics et al. | 544/283 |

FOREIGN PATENT DOCUMENTS

| | | | |
|---|---|---|---|
| 45-499 | 1/1970 | Japan | 544/283 |
| 1201626 | 8/1970 | United Kingdom | 544/283 |

OTHER PUBLICATIONS

Heterocyclic Compounds, CA 57, pp. 829–830.
Quinazoline and 1,4-Benzodiazepines, II, 26, JOC, pp. 1111–1118.
Sternbach, Reeder, Keller & Metlesics, vol. 26, JOC, 4488–4497.
Sternbach and Reeder, vol. 26, JOC, pp. 4936–4941.
1/60 Dehydration of v-Acylaminobenzophenome Oximes, JAC, pp. 475–480.

*Primary Examiner*—Glennon H. Hollrah
*Assistant Examiner*—James H. Turnipseed

*Attorney, Agent, or Firm*—S. R. La Paglia; R. C. Gaffney; S. L. Biggs

[57] ABSTRACT

2-Haloalkyl-3-oxo-4-substituted quinazolines represented by the formula

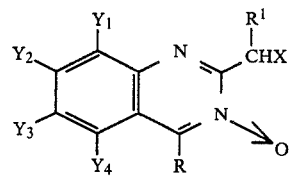

wherein R is hydrogen, lower alkyl, lower alkyl substituted with one to three of the same or different halogens, phenyl or phenyl substituted with 1 to 3 of the same or different substituents selected from a group consisting of lower alkyl, lower alkoxy, lower alkylthio, fluoro, chloro, bromo, iodo, nitro, cyano, or lower alkyl substituted with one to three of the same or different halogens, $R^1$ is hydrogen, lower alkyl, or lower alkyl substituted with one to three of the same or different halogens, $Y_1$, $Y_2$, $Y_3$ and $Y_4$ are independently selected from a group consisting of hydrogen, lower alkyl, lower alkoxy, lower alkylthio, fluoro, chloro, bromo, iodo, nitro, cyano, or lower alkyl substituted with one to three of the same or different halogens and X is fluoro, chloro, bromo, iodo, cyano, lower alkoxy, thiocyano and

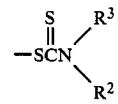

where $R^3$ and $R^2$ are the same or different lower alkyl possess fungicidal and algicidal activity.

4 Claims, No Drawings

ALGICIDAL AND FUNGICIDAL 2-HALOALKYL-3-OXO-4-SUBSTITUTED QUINAZOLINE

BACKGROUND OF THE INVENTION

The present invention pertains to fungicidal and algicidal compounds. In particular, we have been found that 2-haloalkyl-3-oxo-4-substituted quinazolines possess surprisingly good fungicidal and algicidal activity.

The synthesis of 2-chloromethyl-3-oxo-4-phenyl-quinazolines, 2-chloromethyl-3-oxo-4-phenyl-6-chloroquinazoline, 2-methyl-3-oxo-4-phenyl-6-chloroquinazoline, 2-chloromethyl-3-oxo-4-phenyl-6,7-dimethylquinazoline, 6,7-dimethyl-2-dimethylaminomethyl-4-phenylquinazoline-3-oxide, 2-chloromethyl-3-oxo-quinazoline, 2-bromomethyl-3-oxo-4-phenyl-6-chloroquinazoline and the 2-bromopropyl-3-oxo-4-phenyl-6-chloroquinzaoline were reported by Steinbach et al in 82, JACS 475 (1960), 26 JOC 1111 (1961), 26 JOC 4488 (1961) 26 JOC 4936 (1961) and CHEMTECH Nov. 1979, p. 686.

Bell et al report the synthesis of 2-chloromethyl-3-oxo-4-methylquinazoline in CA 57:830(a) and 27 JOC 562 (1962).

The compounds disclosed in the references cited were reported in CHEMTECH Nov. 1979, p. 687 as intermediates in the synthesis of the tranquilizers valium and librium. When tested, the above compounds were reported as possessing rather disappointing activity.

SUMMARY OF THE INVENTION

The 2-haloalkyl-3-oxo-4-substituted quinazolines of the invention are represented by the formula

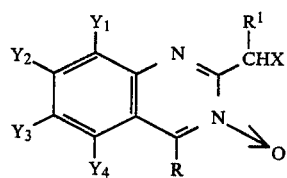

wherein R is hydrogen, lower alkyl, lower alkyl substituted with one to three of the same or different halogens, phenyl or phenyl substituted with 1 to 3 of the same or different substituents selected from a group consisting of lower alkyl, lower alkoxy, lower alkylthio, fluoro, chloro, bromo, iodo, nitro, cyano, or lower alkyl substituted with one to three of the same or different halogens, $R^1$ is hydrogen, lower alkyl, or lower alkyl substituted with one to three of the same or different halogens, $Y_1$, $Y_2$, $Y_3$ and $Y_4$ are independently selected from a group consisting of hydrogen, lower alkyl, lower alkoxy, lower alkylthio, fluoro, chloro, bromo, iodo, nitro, cyano, or lower alkyl substituted with one to three of the same or different halogens and X is fluoro, chloro, bromo, iodo, cyano, lower alkoxy, thiocyano, imidazolyl, and

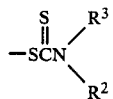

where $R^3$ and $R^2$ are the same or different lower alkyl.

We have found that the quinazolines of this invention are particularly effective as fungicides and algicides.

In part due to their superior fungicidal and algicidal activity, preferred classes of compounds represented by formula I are those wherein R is lower alkyl, X is halogen and $R^1$ is hydrogen or lower alkyl.

Most preferably R is methyl, $R^1$ is hydrogen and $Y_1$, $Y_2$, $Y_3$ and $Y_4$ are all hydrogen.

Definitions

As used herein the following terms have the following meanings, unless expressly stated to the contrary.

The term "alkyl" refers to both straight- and branched-chain alkyl groups. The term "lower alkyl" refers both to straight- and branched-chain alkyl groups of from 1 through 6 carbon atoms and includes primary, secondary, and tertiary alkyl groups. Typical lower alkyls include, for example, methyl, ethyl, n-propyl, isopropyl, n-butyl, t-butyl, n-hexyl and the like.

The term "alkoxy" refers to the group RO- wherein R is alkyl. The term "lower alkoxy" refers to alkoxy groups having from 1 through 6 carbon atoms and includes for example, methoxy, ethoxy, t-butoxy, hexoxy and the like.

The term "alkylthio" refers to the group $R^3S$— wherein R is alkyl. The term "lower alkylthio" refers to alkylthio groups having from 1 through 6 carbon atoms and includes for example, methylthio, ethylthio and the like.

The term "halogen" or "halo atom" refers to the group fluoro, chloro, bromo and iodo.

The term "quinazoline" refers to the group

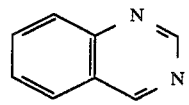

The term 3-oxo-quinazoline refers to the group

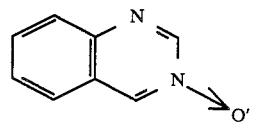

The numbering used herein for this group is as follows:

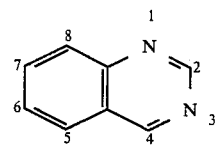

DETAILED DESCRIPTION OF THE INVENTION

The compounds of this invention, represented by formula I, are prepared according to the following scheme:

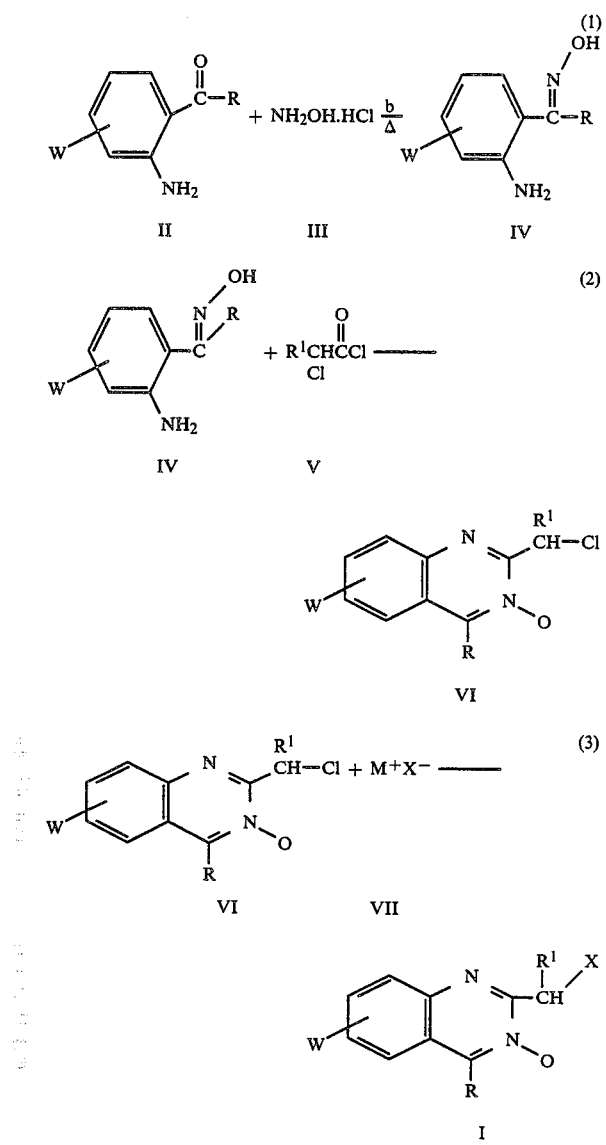

where R, R¹, and X are as defined above, W represents potential further substitution on the aromatic ring, b represents an organic or inorganic base and M represents a monovalent organic or inorganic cation such as a sodium cation, a potassium cation, a dialkylammonium cation and the like.

Reaction (1) is carried out by reacting an appropriate aryl or alkyl-o-aminophenylketone (II) with an essentially equimolar amount of hydroxyamine hydrochloride (III) using an equimolar amount of a base (b) to yield the oxime (IV). Reaction (1) is conducted in an organic solvent such as ethanol, methanol, acetone and the like. The base employed may either be organic or inorganic. Preferably, the base is an organic base such as sodium carbonate, sodium bicarbonate and the like. The reaction is heated at reflux and is generally complete within 1 to 24 hours. Reaction pressure is not critical and for convenience, the reaction pressure is generally atmospheric. The resulting oxime, IV, is isolated and purified by conventional procedures such as extraction, filtration, chromatography, distillation, or alternatively, used in reaction (2) without purification and/or isolation.

The oxime, IV, is next converted to the 2-chloroalkyl-3-oxo-4-substituted quinazoline, VI, by reaction with 2 equivalents of an α-chloro acid chloride, V, as shown in reaction 2 above. The reaction is conducted in a liquid phase using an organic solvent such as acetic acid, propanoic acid and the like. The reaction is generally conducted at a temperature of 0°-100° C. and is generally complete within 1 to 72 hours. Reaction pressure is not critical. For convenience, the reaction pressure is generally atmospheric. The 2-chloroalkyl-3-oxo-4 substituted quinazoline products, VI, are isolated and purified by conventional procedures such as extraction, filtration, chromatography, distillation, or alternatively, is used directly in reaction (3) without purification and/or isolation.

The 2-chloroalkyl-3-oxo-4-substituted quinazoline products, VI, are converted to other 2-substituted alkyl-3-oxo-4-substituted quinazoline by reaction with an appropriate salt as shown in reaction (3) above. The reaction is conducted in a liquid phase using an organic solvent such as methyl ethylketone, acetonitrile, dimethylformamide, ethanol, methanol and the like. When a metallic halide is used in reaction 3, the preferable solvent is ethanol. Whereas, when a dialkyldithiocarbonic acid dialkylammonium salt is used in reaction 3, the preferable solvent is acetonitrile. The reaction is heated at reflux and is generally completed within 1 to 24 hours. Reaction pressure is not critical and for convenience, the reaction pressure is generally atmospheric. The 2-haloalkyl-3-oxo-4-substituted quinazoline products are then isolated and purified by conventional procedures such as extraction, filtration, chromatography, distillation and the like.

Alternatively when X is imidazolyl, the synthesis of the 2-imidazolylalkyl-3-oxo-4-substituted quinazoline is preferably accomplished by reacting the 2-chloroalkyl-3-oxo-4-substituted quinazoline with an essentially equimolar amount of imidazoline and an equimolar amount of a base (b) as shown in reaction (4) below:

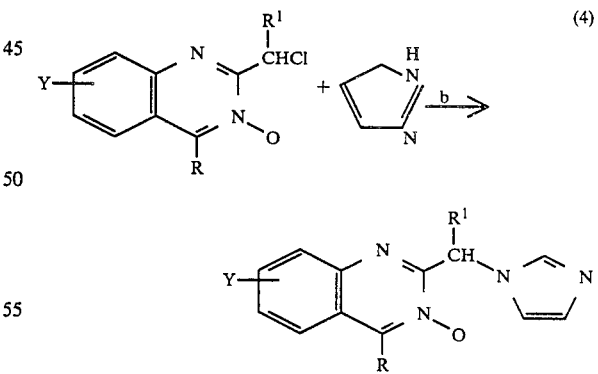

The reaction is conducted in a liquid phase using an organic solvent such as acetonitrile, dimethylformamide and the like. The base employed may be organic or inorganic. Preferably, an inorganic base such as potassium carbonate, potassium bicarbonate or sodium carbonate is employed. The reaction is generally stirred at room temperature and is complete within 1 to 72 hours. Reaction pressure is not critical. For convenience, reaction pressure is atmospheric. The 2-imidazolylalkyl-3-oxo-4-substituted quinazoline products are then isolated and purified by such conventional procedures as extraction, filtration, chromatography, distillation and the like.

UTILITY

The compounds of this invention are useful for controlling fungi, particularly leaf blights caused by such organisms as *Phytophthora infestans conidia, Alternaria solani conidia, Septoria apii*, downy mildew caused by organisms such as *Plasmapara viticola*, bean powdery mildew caused by the organism *Erisiphe polygoni*, and other fungal infections.

However, some fungicidal compounds of the invention may be more fungicidally active than others against particular fungi. Tables III and IV list a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earth, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

The compounds of the invention are also useful for controlling microbiological organisms such as algae, bacteria, molds and occasionally aquatic weeds which foul aqueous industrial effluents and cooling streams, such as those occurring in the paper and food processing industries. They may also be used to control such organisms in other aqueous bodies such as lakes, streams, canals, pools and the like. When so used, a biocidal quantity of one or more of the compounds of this invention is added to the aqueous growth environment of the organisms. Usually, this dosage will range between about 0.1 to 50 ppm. In any given instance, the optimum dosage will depend upon the particular organism and aqueous body involved. For instance, when used to control algae, these compounds will usually be employed at concentrations of about 0.1 to 10 ppm. In terms of pounds of compound per acre of water one foot deep 0.1 to 10 ppm is equal to about 0.3 to 30 pounds per acre of water one foot deep. These compounds may be applied to the aqueous growth environments of such organisms as dispersible powders or in solution with water-miscible solvents.

A further understanding of the invention can be had in the following non-limiting Examples. Wherein, unless expressly stated to the contrary, all temperatures and temperature ranges refer to the Centrigrade system and the term "ambient" or "room temperature" refers to about 20° C.-25° C. The term "percent" or "%" refers to weight percent and the term "mol" or "mols" refers to gram mols. The term "equivalent" refers to a quantity of reagent equal in mols, to the mols of the preceding or succeeding reactant recited in that examples in terms of finite mols or finite weight or volume.

Also, unless expressly stated to the contrary, geometric isomer and racemic mixtures are used as starting materials and correspondingly isomer mixtures are obtained as products.

EXAMPLE 1

Preparation of 2-Acetylaniline Oxime

2-Acetylaniline, 33.8 gm, was added slowly to 300 ml of ethanol containing 18.3 gm of hydroxylamine hydrochloride and 27.7 gm sodium carbonate. After addition of the entire amount of 2-acetylaniline, the system was refluxed for 16 hours and then cooled to room temperature. After cooling, the ethanol was removed by stripping. Water was then added to the residue to give a precipitate. The precipitate was filtered and dried to give a pale yellow solid, m.p. 55°–60° C.

Examination by NMR and IR spectroscopy was in complete accord with the proposed structure.

EXAMPLE 2

Preparation of 2-chloromethyl-3-oxo-4-methylquinazoline

2-Acetylaniline oxime, 14.8 gm, was added to 100 ml of acetic acid and the system was then warmed to 50° C. After warming, 24 gm of chloroacetyl chloride was added dropwise over 2 minutes. The system was heated at 50° C. for an additional 20 minutes and it was then stirred at RT for 16 hours. The acetic acid was removed by stripping to give a yellow solid. The 2-chloromethyl-3-oxo-4-methylquinazoline product was washed with hexane/ether and then dried yielding 16 gm of a brownish-yellow solid, m.p. 162°–164° C.

Examination by NMR and IR spectroscopy was in complete accord with the proposed structure.

EXAMPLE 3

Preparation of the 2-iodomethyl-3-oxo-4-methylquinazoline

2-Chloromethyl-3-oxo-4-methylquinazoline, 2.0 gm, was added to 50 ml of ethanol along with 1.7 gm of potassium iodide. The system was reflux for 8 hours. The ethanol was removed by stripping and the residue dissolved in dichloromethane. The organic solution was washed with water and dried with magnesium sulfate. The dichloromethane was removed by stripping to give a brown solid which was then further purified by washings with hexane/ether. 1.8 gm of the 2-iodomethyl-3-oxo-4-methylquinazoline was recovered, m.p. 123°–133° C.

Examination by NMR and IR spectroscopy was in complete accord with the proposed structure.

EXAMPLE 4

Preparation of the 2-imidazolylmethyl-3-oxo-4-methylquinazoline 2.6 gm of imidazole was added to 50 ml of acetonitrile along with 5.3 gm potassium carbonate. The system was cooled to 0° C. After cooling, 3.3 gm of 2-chloromethyl-3-oxo-4-methylquinazoline in 10 ml of acetonitrile was added dropwise. After addition, the system was allowed to come to room temperature and stirred there for 8 hours. The reaction was then stopped and the reaction solution poured into 30 ml of water. The product was extracted with dichlormethane. The organic solution was treated with charcoal, filtered and then washed with water. The solution was dried with magnesium sulfate and the dichloromethane stripped to give the 2-imidazolylmethyl-3-oxo-4-methylquinazoline as a yellow solid.

Similarily, by following the same procedure as described in Examples 1 to 4 and using the appropriate starting compounds, the following compounds are made:

6-chloro-2-chloromethyl-3-oxo-4-phenylquinazoline;
6-chloro-2-bromomethyl-3-oxo-4-phenylquinazoline;
6-chloro-2-iodomethyl-3-oxo-4-phenylquinazoline;
6-chloro-2-(N,N-dimethyldithiocarbamoylmethyl)-3-oxo-4-phenylquinazoline;
6-chloro-2-(N,N-diethyldithiocarbamoylmethyl)-3-oxo-4-phenylquinazolines;
6-chloro-2-(N,N-diisopropyldithiocarbamoylmethyl)-3-oxo-4-phenylquinazoline;
2-iodomethyl-3-oxo-4-(4-chlorophenyl)quinazoline;
6-chloro-2-(1-thiocyanoethyl)-3-oxo-4-phenylquinazoline;
6-chloro-2-(1-iodoethyl)-3-oxo-4-phenylquinazoline;
2-chloromethyl-3-oxo-4-(4-chlorophenyl)quinazoline;
2-chloromethyl-3-oxo-4-methylquinazoline;
2-bromomethyl-3-oxo-4-methylquinazoline;
2-iodomethyl-3-oxo-4-methylquinazoline;
2-cyanomethyl-3-oxo-4-methylquinazoline;
2-thiocyanomethyl-3-oxo-4-methylquinazoline;
2-imidazolylmethyl-3-oxo-4-methylquinazoline;
2-(N,N-diethyldithiocarbamoylmethyl)-3-oxo-4-methylquinazoline;
2-(methylthio-t-butoxy)-3-oxo-4-methylquinazoline;
2-(1-chloroethyl)-3-oxo-4-methylquinazoline;
2-(1-imidazolylethyl)-3-oxo-4-methylquinazoline;
2-(N,N-diethyldithiocarbamoylmethyl)-3-oxo-4-methylquinazoline;
2-thiomethyl-3-oxo-4-methylquinazoline;
2-(methyl-2,5-dichlorophenoxy)-3-oxo-4-methylquinazoline;
6-bromo-2-chloromethyl-3-oxo-4-phenylquinazoline;
6,7-dimethyl-2-chloromethyl-3-oxo-4-phenylquinazoline;
6-iodo-2-chloromethyl-3-oxo-4-methylquinazoline;
6,7-dimethyl-2-chloromethyl-3-oxo-4-methylquinazoline;
6,7-dimethoxy-2-iodomethyl-3-oxo-4-methylquinazoline;
5,8-dimethoxy-2-chloromethyl-3-oxo-4-methylquinazoline;
6,7-(di-trifluoromethyl)-2-chloromethyl-3-oxo-4-methylquinazoline;
6-methylthio-2-chloromethyl-3-oxo-4-methylquinazoline;
6-cyano-2-chloromethyl-3-oxo-4-methylquinazoline;
6-chloro-2-(1-chloropropyl)-3-oxo-4-methylquinazoline;
6-chloro-2-(1-chloropropyl)-3-oxo-4-phenylquinazoline;
2-chloromethyl-3-oxo-4-ethylquinazoline;
2-chloromethyl-3-oxo-4-isopropylquinazoline;
2-chloromethyl-3-oxo-4-trifluoromethylquinazoline;
2-chloromethyl-3-oxo-4-(2,2,2-trichloroethyl)quinazoline;
2-chloromethyl-3-oxo-4-(1,3-dibromophenyl)quinazoline;
2-chloromethyl-3-oxo-4-(1,3-diiodophenyl)quinazoline;
2-(1-chloroisopropyl)-3-oxo-4-methylquinazoline;
5,6,7,8-tetrachloro-2-chloromethyl-3-oxo-4-methylquinazoline;

2-chloromethyl-3-oxo-4-(1,3-dimethylphenyl)quinazoline;
2-chloromethyl-3-oxo-4-(2,4-dimethoxyphenyl)quinazoline;
2-chloromethyl-3-oxo-4-(2,6-diethylphenyl)quinazoline;
2-chloromethyl-3-oxo-4-(3,5-diethoxyphenyl)quinazoline;
2-chloromethyl-3-oxo-4-(4-trifluoromethylphenyl)quinazoline;
2-chloromethyl-3-oxo-4-(4-methylthiophenyl)quinazoline; and
2-chloromethyl-3-oxo-4-(4-cyanophenyl)quinazoline;

EXAMPLE 5

Mycelial Inhibition

A number of the compounds of the present invention were evaluated for in vitro fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were inoculated with the particular mycelium growth by covering the paper with a potato dextrose broth culture of mycelial suspension. The inoculated papers were then placed on potato dextrose agar plates and sprayed by means of a microsprayer with the fungicidal solution. The treated paper strips were incubated at 25° C. and the data is taken after 24 hours. Fungicidal activities are measured by a zone of inhibited mycelial growth from the center of the paper strip. The effectiveness of the compounds tested for fungicidal activity is reported in Table IV for those compounds which were effective in inhibiting mycelial growth. The activity is reported in terms of the micrograms/cm$^2$ for 99% control of the fungus.

EXAMPLE 6

Tomato Late Blight

Compounds of the invention were tested for the control of the Tomato Late Blight organism *Phytophthora infestans conidia*. Five- to six-week-old tomato (variety Bonny Best) seedlings were used. The tomato plants were sprayed with a 250 ppm solution of the test compound in acetone, water and a small amount of a non-ionic emulsifier. The sprayed plants were then inoculated one day later with the organism, placed in an environmental chamber and incubated at 66°-68° F. and 100% relative humidity for at least 16 hours. Following the incubation, the plants were allowed to dry and then were maintained in a greenhouse for approximately 7 days. The percent disease control provided by a given test compound was based on the percent disease reduction relative to untreated check plants. The compounds giving effective control at the test concentration are tabulated in Table III.

EXAMPLE 7

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250 ppm solution of the test compound in an acetone-and-water solution containing a small amount of a non-ionic emulsifier. The sprayed plants were inoculated one day later with the organism, placed in the environment chamber and incubated at 66° to 68° F. and 100% relative humidity for 24 hours. Following the incubation, the plants were maintained in a greenhouse for about 12 days. Percent disease control was based on the percent disease development on untreated check plants. The compounds giving effective control at the test concentration are tabulated in Table III.

EXAMPLE 8

Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a non-ionic emulsifier. The plants were then inoculated with the organism and placed in an environmental chamber and incubated at 66°-68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The compounds giving effective control at the test concentrations are reported in Table III.

EXAMPLE 9

Grape Downy Mildew Control

The compounds of the invention were tested for the control of Grape Downy Mildew organism *Plasmapara viticola*. Detached leaves, between 70 mm and 85 mm in diameter, of 7-week-old *Vitis vinifera cultivar* Emperor grape seedlings were used as hosts. The leaves were sprayed with a solution of the test compound in acetone. The sprayed leaves were dried, inoculated with a spore suspension of the organism, placed in a humid environmental chamber and incubated at 66° to 68° F. and about 100% relative humidity. After incubation for two days, the plants were then held in a greenhouse for seven to nine days, then, the amount of disease control was determined. The percent disease control provided by a given test compound was based on the percent disease reduction to untreated check plants. The results are tabulated in Table III.

EXAMPLE 10

Alga Control

Representative compounds of the invention were tested as aquatic herbicides and algicides by the following method. The weed test species were Lemna, *Elodea canadensis*, and the algae used was *Spirolina maxima*.

An acetone solution of the test compound and a small amount of an alkylarylpolyoxyethylene glycol-containing surfactant was prepared. This solution was mixed with a nutrient broth in quantity sufficient to give a concentration of 2 ppm. Eight ounce plastic cups were filled with 150 ml of this solution. A sample of the test, Lemna and Elodea, was added to each cup. Forty ml of Spirolina culture with the 2 ppm treatment was placed in 1½ ounce plastic cups. The containers were then placed in an illuminated environment maintained at a temperature of about 20° C. for incubation. The containers were observed periodically for growth (as compared to an untreated check). The effectiveness of the test compound was determined based on a final observation of growth after 7 to 10 days. The results of the test on a 0-to-100 basis—0 indicating no effectiveness and 100 indicating complete effectiveness—are reported in Table V.

TABLE I

COMPOUNDS OF THE FORMULA

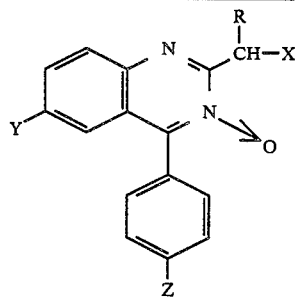

| Comp. # | R | X | Y | Z | Carbon Calc. | Carbon Fd. | Hydrogen Calc. | Hydrogen Fd. | Nitrogen Calc. | Nitrogen Fd. | | M.P. |
|---|---|---|---|---|---|---|---|---|---|---|---|---|
| 1 | H | Cl | Cl | H | 59.00 | 59.15 | 3.30 | 3.56 | 9.20 | 9.21 | yellow powder | 121–124° C. |
| 2 | H | Br | Cl | H | 51.50 | 56.10 | 2.88 | 3.30 | 8.01 | 7.71 | brown solid | 108–116° C. |
| 3 | H | I | Cl | H | 45.4 | 49.3 | 2.54 | 3.06 | 7.06 | 7.49 | brown solid | 110–125° C. |
| 4 | H | $\underset{\text{SCN(CH}_3)_2}{\overset{\text{S}}{\|}}$ | Cl | H | 55.40 | 56.29 | 4.10 | 4.31 | 10.80 | 10.84 | off-white powder | 202–204° C. |
| 5 | H | I | H | Cl | 45.40 | 46.10 | 2.54 | 2.90 | 2.06 | 2.25 | yellow solid | 174–180° C. |
| 6 | H | $\underset{\text{SCN(Et)}_2}{\overset{\text{S}}{\|}}$ | H | H | 65.4 | 65.2 | 5.76 | 5.68 | 11.4 | 11.8 | tan solid | 143–148° C. |
| 7 | H | $\underset{\text{SCN(i-pr)}_2}{\overset{\text{S}}{\|}}$ | H | H | 66.9 | 66.8 | 6.39 | 6.43 | 10.7 | 10.9 | brown solid | 116–123° C. |
| 8 | CH₃ | SCN | Cl | H | 59.7 | 56.9 | 3.54 | 3.57 | 12.3 | 12.3 | yellow solid | 153–155° C. |
| 9* | CH₃ | I | Cl | H | — | — | — | — | — | — | yellow solid | 144–148° C. |
| 10 | H | Cl | H | Cl | 59.0 | 58.38 | 3.3 | 3.4 | 9.2 | 9.78 | yellow powder | 168–171° C. |

*Compound 9 loses iodine during analysis.

TABLE II

COMPOUNDS OF THE FORMULA

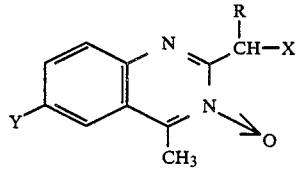

| Comp. # | R | X | Y | Carbon Calc. | Carbon Fd. | Hydrogen Calc. | Hydrogen Fd. | Nitrogen Calc. | Nitrogen Fd. | | M.P. |
|---|---|---|---|---|---|---|---|---|---|---|---|
| 11 | H | Cl | H | 57.87 | 60.85 | 4.35 | 5.0 | 13.43 | 14.05 | light gold powder | 162–164° C. |
| 12 | H | Br | H | 47.4 | 43.5 | 3.58 | 4.2 | 11.10 | 11.5 | brown solid | >200° C. |
| 13 | H | I | H | 40.0 | 40.5 | 3.02 | 3.17 | 9.34 | 9.63 | brown solid | 123–133° C. |
| 14 | H | CN | H | 66.3 | 61.8 | 4.55 | 5.15 | 21.1 | 15.6 | orange solid | >200° C. |
| 15 | H | SCN | H | 57.1 | 56.7 | 3.92 | 3.91 | 18.2 | 18.3 | cream solid | >147–150° C. |
| 16 | H | N N | H | 64.9 | 63.6 | 5.03 | 5.87 | 23.3 | 24.1 | yellow solid | >200° C. |
| 17 | H | $\underset{\text{SCN(Et)}_2}{\overset{\text{S}}{\|}}$ | H | 56.0 | 56.14 | 6.0 | 6.83 | 13.1 | 12.15 | off-white solid | 132–136° C. |
| 18 | H | SC(CH₃)₃ | H | 64.1 | 58.1 | 6.92 | 6.7 | 10.7 | 11.8 | brown solid | — |
| 19 | CH₃ | Cl | H | 59.3 | 60.28 | 5.0 | 5.39 | 12.6 | 12.96 | yellow needles | 175–178° C. |

TABLE II-continued
COMPOUNDS OF THE FORMULA

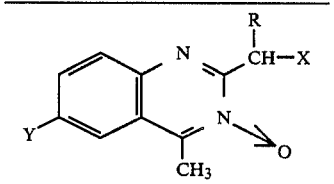

| Comp. # | R | X | Y | Carbon Calc. | Carbon Fd. | Hydrogen Calc. | Hydrogen Fd. | Nitrogen Calc. | Nitrogen Fd. | | M.P. |
|---|---|---|---|---|---|---|---|---|---|---|---|
| 20 | $CH_3$ | -N⟨imidazole⟩ | H | 66.13 | 64.7 | 5.55 | 5.72 | 22.03 | 20.5 | mustard solid | 143–154° C. |
| 21 | $CH_3$ | $SCN(Et)_2$ (C=S) | H | 57.3 | 57.88 | 6.3 | 6.51 | 12.5 | 12.58 | off-white solid | 133–135° C. |
| 22 | H | SH | H | 58.2 | 61.7 | 4.89 | 4.96 | 13.6 | 14.3 | mustard solid | 170–185° C. |
| 23 | H | -O-(2,5-diClPh) | H | 57.33 | 58.21 | 3.61 | 3.71 | 8.36 | 8.41 | cream solid | 175–178° C. |

TABLE III

| Comp. # | Grape Downy Mildew | Tomato Late Blight | Celery Late Blight | Tomato Early Blight |
|---|---|---|---|---|
| 1 | 88 | 50 | 39 | 90 |
| 2 | 89 | 0 | 23 | 23 |
| 3 | 35 | 0 | 33 | 0 |
| 4 | 0 | 0 | 0 | 0 |
| 5 | 0 | 0 | 23 | 50 |
| 6 | 6 | 0 | 0 | 0 |
| 7 | 0 | 29 | 0 | 11 |
| 8 | 0 | 18 | 29 | 0 |
| 9 | 67 | 0 | 0 | 77 |
| 10 | 96 | 29 | 62 | 11 |
| 11 | 0 | 57 | 8 | 6 |
| 12 | 84 | 94 | 56 | 44 |
| 13 | 99 | 39 | 71 | 0 |
| 14 | 0 | 0 | 14 | 8 |
| 15 | 6 | 0 | 0 | — |
| 16 | 0 | 0 | 29 | 57 |
| 17 | 35 | 0 | 90 | 27 |
| 18 | 0 | 11 | 0 | 0 |
| 19 | 64 | 0 | 98 | 0 |
| 20 | 13 | 4 | 17 | 0 |
| 21 | 0 | 0 | 0 | 37 |
| 22 | 0 | 0 | 44 | 0 |
| 23 | 35 | 39 | — | 57 |

TABLE IV

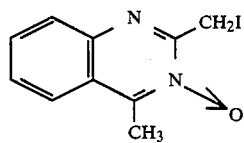

| | % Control |
|---|---|
| Pythium | 66% |
| Botrytis | 94% |
| Asper. | 100% |
| Xantho. | 88% |
| GDM | 99% |
| TLB | 39% |

TABLE IV-continued

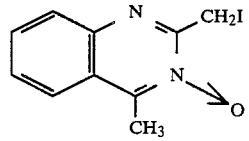

| | % Control |
|---|---|
| CLB | 71% |
| RB | 28% |

TABLE V

| Comp. # | Spirolina | Lemna | Elodea |
|---|---|---|---|
| 1 | 48 | 0 | 65 |
| 2 | 80 | 0 | 0 |
| 3 | 80 | 0 | 0 |
| 8 | 50 | 0 | 0 |
| 11 | 85 | 65 | 80 |
| 12 | 80 | 95 | 80 |
| 14 | 30 | 0 | 0 |
| 19 | 0 | 0 | 65 |

We claim:

1. A method for the control of fungi which comprises contacting said fungi or their growth environment with a fungicidally effective amount of a compound of the formula

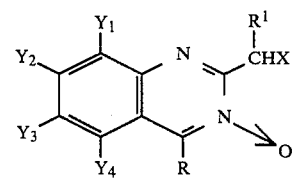

wherein R is hydrogen, lower alkyl, lower alkyl substituted with one to three of the same or different halogens, phenyl or phenyl substituted with 1 to 3 of the same or different substituents selected from a group consisting of lower alkyl, lower alkoxy, lower alkylthio, fluoro, chloro, bromo, iodo, nitro, cyano, or lower alkyl substituted with one or three of the same or different halogens, $R^1$ is hydrogen, lower alkyl, or lower alkyl substituted with one to three of the same or different halogens, $Y_1$, $Y_2$, $Y_3$ and $Y_4$ are independently selected from a group conisting of hydrogen, lower alkyl, lower alkoxy, lower alkylthio, fluoro, chloro, bromo, iodo, nitro, cyano, or lower alkyl substituted with one to three of the same or different halogens and X is fluoro, chloro, bromo, iodo, cyano, lower alkoxy, thiocyano and

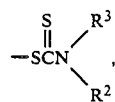

where $R^3$ and $R^2$ are the same or different lower alkyl; or mixtures of such compounds.

2. The method of claim 1 wherein X is fluoro, bromo, or iodo.

3. The method of claim 1 where in R is methyl, $R^1$ is hydrogen, X is iodo and $Y_1$, $Y_2$, $Y_3$ and $Y_4$ are hydrogen.

4. The method of claim 1 wherein R is lower alkyl or lower alkyl substituted with one to three of the same or different halogens.

* * * * *

UNITED STATES PATENT AND TRADEMARK OFFICE
CERTIFICATE OF CORRECTION

PATENT NO.  : 4,753,943
DATED       : June 28, 1988
INVENTOR(S) : William F. King Et Al.

It is certified that error appears in the above-identified patent and that said Letters Patent are hereby corrected as shown below:

Claim 1, Col. 15, line 7, "one or three" should read --one to three--.

Signed and Sealed this

Twenty-eighth Day of February, 1989

*Attest:*

DONALD J. QUIGG

*Attesting Officer*     *Commissioner of Patents and Trademarks*